United States Patent [19]

Kapur et al.

[11] Patent Number: 5,053,501
[45] Date of Patent: Oct. 1, 1991

[54] PREPARATION OF 3-EXOMETHYLENECEPHAM SULFOXIDES AND 2-CHLOROSULFINYLAZETIDINONES USING MOLECULAR SIEVES

[75] Inventors: Jagdfish C. Kapur, Delft; Jan J. De Koning, Rijswijk; Roland P. Bezemer, Delft, all of Netherlands

[73] Assignee: Gist-Brocades N. V., Delft, Netherlands

[21] Appl. No.: 497,541

[22] Filed: Mar. 21, 1990

Related U.S. Application Data

[63] Continuation-in-part of Ser. No. 384,988, Jul. 24, 1989, abandoned.

[30] Foreign Application Priority Data

Mar. 22, 1989 [EP] European Pat. Off. ........ 89200718.8

[51] Int. Cl.$^5$ ............... C07D 205/095; C07D 501/10; C07B 45/04
[52] U.S. Cl. .................................... 540/218; 540/359
[58] Field of Search ................ 540/359, 218

[56] References Cited

U.S. PATENT DOCUMENTS 4,081,440 3/1978 Kukolja .............................. 540/359
4,190,724 2/1980 Chon .................................. 540/215

Primary Examiner—Mark L. Berch
Attorney, Agent, or Firm—Bierman and Muserlian

[57] ABSTRACT

3-Exomethylenecepham sulfoxide derivatives and intermediates therefor, viz. 2-chlorosulfinylazetidin-4-ones are prepared in high yield and purity by reaction of a penam sulfoxide ester with a N-chloro halogenating agent in the presence of molecular sieves.

13 Claims, No Drawings

PREPARATION OF 3-EXOMETHYLENECEPHAM SULFOXIDES AND 2-CHLOROSULFINYLAZETIDINONES USING MOLECULAR SIEVES

PRIOR APPLICATION

This application is a continuation-in-part of U.S. patent application Ser. No. 384,988 filed July 24, 1989, now abandoned.

The invention relates to an improved process for the preparation of 3-exomethylenecepham sulfoxide derivatives and intermediates therefor, viz. 2-chlorosulfinylazetidin-4-ones.

Cephalosporins bearing a 3-exomethylene group (also referred to hereinafter as a 3-methylene group) are valuable intermediates in the synthesis of cephalosporins having antibacterial activity. For example, 3-methylenecepham sulfoxide (also named 3-methylene-1-oxo-cepham) can be converted into 3-halo-3-cephem antibiotics. One such 3-chloro-3-cephem compound is known commercially as cefaclor.

2-Chlorosulfinylazetidin-4-ones in their turn can be converted into valuable intermediate 3-methylene sulfoxide derivatives.

Several routes are known for the synthesis of 3-methylenecepham compounds. These routes can be divided in two groups, one starting from cephem and the other from penam compounds.

The first group is almost entirely limited to the preparation of 3-methylenecepham sulfides. However, two methods for the reduction of 3-substituted methylcephem sulfoxides have been described in the literature:
a) The first involves the use of metals with a low oxidation number as reducing agent. For example, Synth. Comm. 16, 649–652 (1986) describes the preparation of 3-methylene-1-oxo-cepham compounds by reduction of the corresponding 3-acetoxymethyl cephem compounds with activated zinc dust and ammonium chloride, in a yield of 50–80% (no purity mentioned).
b) The second is carried out via 3-phosphoniomethyl-3-cephem derivatives. For example EP-A-0299587 discloses a process for the preparation of 3-methylenecepham derivatives, including the corresponding sulfoxides (in a yield of 50–95%), via 3-phosphoniomethyl-3-cephem derivatives; these, in turn, can be prepared from 3-halomethyl-3-cephem derivatives.

An example of a process from the second group is the ring expansion of a penicillin sulfoxide ester via a 2-chlorosulfinylazetidin-4-one. This two-step process is illustrated by the following generalized reaction scheme:

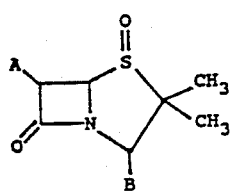

N-chloro halogenating agent
—————————————————→

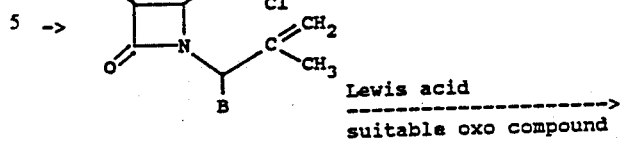

Lewis acid
—————————————→
suitable oxo compound

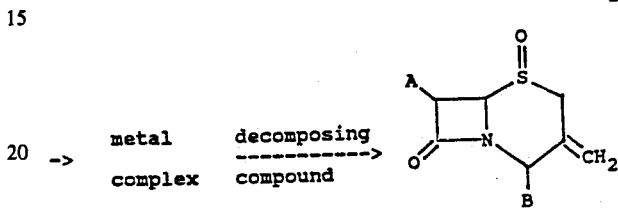

metal        decomposing
—————→
complex      compound

According to BE-A-879211 this process may be optimized by using an insoluble poly-(4-vinylpyridine)-divinylbenzene crosslinked co-polymer as a hydrogen chloride binding agent, together with the N-chloro halogenating agent. U.S. Pat. No. 4,190,724 discloses that this process may be advantageously carried out by decomposing with a suitable decomposing hydroxy compound the metal 2-chlorosulfinylazetidin-4-one oxo complex, formed after the addition of the Lewis acid and oxo compound.

It has now surprisingly been found that a substantially higher yield and purity of the 3-methylenecepham sulfoxide derivatives may be achieved if, instead of the copolymer as described in BE-A-879211, molecular sieves are used.

Accordingly, the present invention provides a process for the preparation of a 2-chlorosulfinylazetidin-4-one of formula II

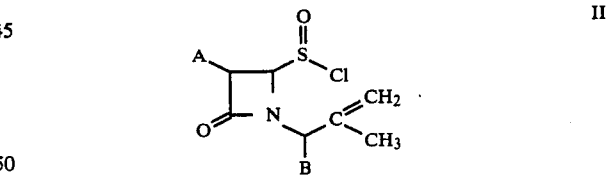

wherein
A is a protected amino group and
B is a protected carboxy group,
by reacting a corresponding penam sulfoxide ester of the general formula III

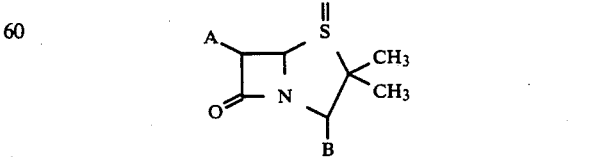

wherein A and B are as defined above, with an N-chloro halogenating agent, in the presence of molecular sieves.

Either or both of the groups A and B in formula I and/or II may be converted consequently to a deprotected amino group or a deprotected carboxy group. Any conventional method for effecting such a conversion may be employed.

The molecular sieves may be activated or not, but are preferably activated. These are typically used in the form of a powder, usually having a nominal pore diameter of from about $2 \times 10^{-4}$ to about $12 \times 10^{-4}$ μm, typically about $3 \times 10^{-4}$ μm or about $4 \times 10^{-4}$ μm or about $5 \times 10^{-4}$ μm or about $10 \times 10^{-4}$ μm, preferably about $4 \times 10^{-4}$ μm.

The amount of molecular sieves used is usually from about 2.5–40% (w/w), preferably from about 5–25% (w/w) and more preferably from about 7–8% (w/w) in relation to the penam sulfoxide ester starting material.

Preferably the molecular sieves as indicated above are saturated with water. Also molecular sieves partially saturated with water may be used. This is more surprising because in the prior art the importance of the dryness of the process has been emphasized. In a further aspect of the invention, the compound of formula II is converted into a 3-methylenecepham derivative of formula I,

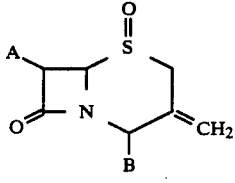

wherein A and B are as defined above. Any conventional method for effecting such a conversion may be employed.

Moreover, it has also surprisingly been found that these preparations in the presence of molecular sieves advantageously can be carried out in one pot, without removing said molecular sieves and other insoluble material. Such a one-pot process has not been described for the above-indicated process disclosed in BE-A-879211.

Therefore, in another aspect of the invention, a one-pot process for the preparation of a 3-methylenecepham derivative of formula I or a pharmaceutically acceptable salt thereof

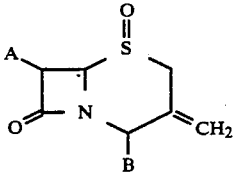

is provided,
wherein A and B are as defined above, which comprises reacting a corresponding penam sulfoxide of the general formula III

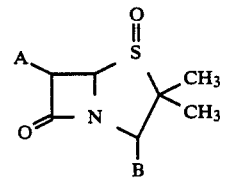

wherein A and B are as defined above, with an N-chloro halogenating agent, in the presence of molecular sieves, adding a suitable oxo compound and a suitable Lewis acid, isolating the resulting complex, and then decomposing the same by adding a suitable alcohol.

In a preferred embodiment, the compound of formula III is 4-nitrobenzyl 2,2-dimethyl-1-oxo-6-phenoxyacetamidopenam-4-carboxylate or 4-nitrobenzyl 2,2-dimethyl-1-oxo-6-phenylacetamidopenam-4-carboxylate, which gives rise to 4-nitrobenzyl 3-methylene-1-oxo-7-phenoxyacetamidocepham-4-carboxylate and 4-nitrobenzyl 3-methylene-1-oxo-7-phenylacetamidocepham-4-carboxylate, respectively.

The highest yields known from the prior art for the preparation of 4-nitrobenzyl 3-methylene-1-oxo-7-phenoxyacetamidocepham-4-carboxylate and of 4-nitrobenzyl 3-methylene-1-oxo-7-phenylacetamidocepham-4-carboxylate, disclosed in U.S. Pat. No. 4,190,724, were 71.1% (and a purity of 97.3%) or 76.2% (no purity mentioned) and 59.3% (no purity mentioned).

With the use of molecular sieves according to this invention, however, 4-nitrobenzyl 3-methylene-1-oxo-7-phenoxyacetamidocepham-4-carboxylate and 4-nitrobenzy 3-methylene-1-oxo-7-phenylacetamidocepham-4-carboxylate may be prepared with a yield of 83.9% (and a purity of 98.2%) and with a yield of 70.9% (and a purity of 97.5%), respectively.

With the use of molecular sieves partially or fully saturated with water according to this invention, 4-nitrobenzyl 3-methylene-1-oxo-7-phenoxyacetamidocepham-4-carboxylate and 4-nitrobenzyl 3-methylene-1-oxo-7-phenylacetamidocepham-4-carboxylate may be prepared with a yield of 85.0% (and a purity of 98.5%) and with a yield of 76.7% (and a purity of 97.0%), respectively.

These preparations with molecular sieves may be carried out in a one-pot process, with also higher yields than the processes known from the prior art. According to the present invention 4-nitrobenzyl 3-methylene-1-oxo-7-phenoxyacetamidocepham-4-carboxylate may be obtained with a yield of 79.9% (and a purity of 97.0%) and 4-nitrobenzyl 3-methylene-1-oxo-7-phenylacetamidocepham-4-carboxylate may be obtained with a yield of 73.0% (and a purity of 94.5%).

Without using molecular sieves in these preparations non-reproducible results with a much lower yield were obtained.

Another advantage of the process according to this invention is that molecular sieves are much cheaper and less detrimental to the surroundings than polyvinyl pyridine copolymers. Moreover, it is sufficient to use molecular sieves in an amount of about 7.5% (w/w) relating to the penam sulfoxide ester. This is much less than the polyvinyl pyridine co-polymer, which is described in BE-A-879211 as being used in an amount of about 50% (w/w) relating to the penam sulfoxide ester. The use of molecular sieves partially or fully saturated with water gives the extra advantage of easier winning back the molecular sieves, without the need for drying the same for recycling in the process.

Conventional methods for effecting the conversion from a compound of formula II into a compound of formula I are for instance: reacting a compound of formula II with a Lewis acid type Friedel-Crafts catalyst, a Bronsted proton acid type Friedel-Crafts catalyst or a metathetic cation-forming agent in a dry inert organic solvent, or dissolving such compound in a Bronsted acid. E     ples include the Lewis acids and Bronsted acids mentioned in U.S. Pat. No. 4,052,387.

Conventional methods for effecting the deprotecting of groups A and B in formula I and/or II are, for instance, acid or basic hydrolysis or hydrogenolysis.

Suitable protected amino groups for the group A include amino groups substituted with a protecting group at positions 7 and 6, respectively. Examples include acylamino, phenyl(lower)alkylamino, (cyclo)alkylamino and (cyclo)alkylideneamino groups, and the like.

Suitable acylamino groups include aliphatic, aromatic and heterocyclic acylamino groups, the acyl group being for example formyl, acetyl, propionyl, butyryl, valeryl, hexanoyl, methoxycarbonyl, ethoxycarbonyl, t-butoxycarbonyl, phenoxycarbonyl, benzoyl, toluyl, phenylpropionyl, in particular phenylacetyl and phenoxyacetyl. Basically the same groups mentioned in U.S. Pat. No. 4,190,724, and other groups known to persons skilled in the art of cephalosporin and penicillin chemistry, are suitable.

Suitable protected carboxy groups for the group B include carboxy groups substituted with a suitable protecting group conventionally used in cephalosporin and penicillin chemistry at positions 4 and 3, respectively.

Suitable examples of such protected carboxy groups include esters, such as methyl ester, ethyl ester, propyl ester, butyl ester, benzyl ester; and optionally substituted esters such as diphenylmethyl ester and in particular 4-nitrobenzyl ester. U.S. Pat. No. 4,190,724 referred to above, discloses suitable examples.

The N-chloro halogenating agent is typically an N-haloimide such as N-chlorophthalimide or N-chlorosuccinimide.

Suitable Lewis acids include stannic, aluminium, zinc, antimony, titanium, ferric, gallium, zirconium, mercuric and chromium halide, and combinations thereof. Examples include the Lewis acids mentioned in U.S. Pat. No. 4,052,387.

Suitable oxo compounds include, for instance ethers, in particular diethyl ether and ketones. Examples include the oxo compounds mentioned in U.S. Pat. No. 4,190,724.

Suitable decomposing compounds are hydroxy-containing compounds, for example lower alcohols such as methanol. Any of the decomposing compounds mentioned in U.S. Pat. No. 4,190,724 may be used.

Examples of pharmaceutically acceptable salts of the compounds of formula I and II include conventional non-toxic salts such as alkali metal salts (e.g. sodium salt, potassium salt, etc.) alkaline earth metal salts (e.g. calcium salt, magnesium salt, etc.), ammonium salts, organic base salts (e.g. trimethylamine salt, triethylamine salt, pyridine salt, picoline salt, dicyclohexylamine salt, N,N'-dibenzylethylenediamine salt), organic acid salts (e.g. acetate, maleate, tartrate, methanesulfonate, cinnamate, p-chlorocinnamate, benzenesulfonate, formate, toluenesulfonate), inorganic acid salts (e.g. hydrochloride, hydrobromide, hydroiodide, sulfate, phosphate) or a salt with an amino acid (e.g. arginine, aspartic acid, glutamic acid), and the like.

The reaction conditions are not very critical and may be optimized experimentally. The reaction of the penam sulfoxide ester with the N-chloro halogenating agent in the presence of molecular sieves preferably is carried out at reflux temperatures, preferably during 40–120 minutes, more preferably during about 80 to about 100 minutes, in an organic solvent. The resulting suspension is cooled to between about 0° C. and about 20° C., preferably to about 10° C. and optionally filtered to remove the molecular sieves and other insoluble material such as, for instance, phthalimide if using N-chlorophthalimide as N-chloro halogenating agent. The cold filtrate is reacted with a suitable oxo agent, as for instance diethyl ether, and a Lewis acid, followed by stirring for between about 2 and about 24 hours, at a temperature between about −25° C. and about 45° C. After removing the organic solvent from the metal complex for instance by centrifugation and/or decantation and washing, the decomposition reaction with for instance methanol is carried out.

The following Examples further illustrate the invention.

GENERAL PROCEDURES a. Purities of $\beta$-lactam products have been determined through NMR spectroscopy/HPLC analysis using an internal standard.

b. High Performance Liquid Chromatography
Column: CHROMPACK 10 cm cartidge cat. No. 28267, particle size 5 $\mu$m, reversed phase c 18.
Column solvent: 570 ml phosphate buffer pH 6 + 430 ml acetonitrile.
Rate: 0.8 ml/minute.
Sample: $\pm 10$ mg per 25 ml of acetonitrile.

c. Infrared spectra were determined on a Perkin-Elmer spectrophotometer. $^1$H-NMR and $^{13}$C-NMR spectra were measured on a Brucker AM 360 MHz spectrometer. Mass spectra were recorded on a Varian MAT 311A spectrophotometer.

d. The properties of the molecular sieves used have been mentioned in Reagents for Organic Synthesis, Fieser and Fieser, Vol. I, John Wiley and Sons, Inc., New York, first edition, 1968, pages 703–705.

EXAMPLE 1

Preparation of 4-nitrobenzyl 3-exomethylene-1-oxo-7-phenylacetamidocepham-4-carboxylate 4-Nitrobenzyl 2,2-dimethyl-1-oxo-6-phenylacetamidopenam-4-carboxylate (1.936 g; purity by HPLC=98.5%), N-chlorophthalimide (0.761 g) and molecular sieves (4A, activated powder, max. grain size 50 $\mu$m; 0.147 g, Janssen Chimica) in dry toluene (37 ml) were quickly heated to reflux for about 100 minutes. The reaction mixture was cooled to about 10° C. and further stirred at the same temperature for 10 minutes. The cold suspension was filtered and the residue washed with dry toluene. The combined filtrate was cooled to about −5° to −8° C., treated with dry ether (2 ml), followed by slow addition of stannic chloride (1 ml). The complex, thus formed, was stirred for about 30 minutes at about −5° to −8° C. and then for about 16 hours at room temperature.

The complex was centrifuged, washed with dry toluene (10 ml) and then with reagent grade n-hexane (10 ml). The complex was then slowly added to stirred methanol (about 25 ml) which resulted in the formation of 4-nitrobenzyl 3-exomethylene-1-oxo-7-phenylacetamidocepham-4-carboxylate. The above suspension was stirred for about 4 hours under ice-bath cooling, filtered, washed with methanol and ether, respectively, and dried in vacuo to a constant weight. 1.38 g of 4-Nitrobenzyl 3-exomethylene-1-oxo-7-phenylacetamidocepham-4-carboxylate with a purity by HPLC of 97.5% was isolated. The yield was therefore 70.9%.

IR Spectrum (KBr): 3320, 1765, 1740, 1640, 1610, 1520, 1350, 1200, 1030, 740, 725 cm$^{-1}$.

$^1$H NMR (360 MHz, DMSO-d$_6$, δ-values in ppm, TMS): 3.65, 3.78 (AB$_q$, 2H, CH$_2$, C$_6$H$_5$); 3.82, 4.00 (AB$_q$, 2H, C$^2$H$_2$); 5.13 (d, 1H, C$^6$H); 5.47 (s, 2H, CH$_2$C$_6$H$_4$NO$_2$(p)); 5.53, 5.63, 5.88 (3s, 3H, =CH$_2$+C$^4$H); 5.76 (dd, 1H, C$^7$H); 7.42 (m, 5H, C$_6$H$_5$); 7.78, 8.37 (AB$_q$, 4H, CH$_2$C$_6$H$_4$NO$_2$(p)); 8.29 (d, 1H, NH). $^{13}$C NMR (90 MHz; DMSO-d$_6$; ppm): 42.0 (—CH$_2$Ar); 49.2 (C$^2$); 55.3, 59.0 (C$^7$, C$^4$); 66.0 (OCH$_2$); 66.1 (C$^6$); 125.7 (=CH$_2$).

Mass Spectrum: CI(NH$_3$) gave MH$^+$=484 and M(NH$_4$)$^+$=501.

EXAMPLE 2

Preparation of 4-nitrobenzyl 3-exomethylene-1-oxo-7-phenoxyacetamidocepham-4-carboxylate 4-Nitrobenzyl 2,2-dimethyl-1-oxo-6-phenoxyacetamidopenam-4-carboxylate (2.0 g; purity by HPLC=99.3%), N-chlorophthalimide (0.772 g) and molecular sieves (4A, activated powder, max. grain size 50 μm; 0.150 g, Janssen Chimica) in dry toluene (37 ml) were quickly heated to reflux for about 100 minutes. The reaction mixture was cooled to about 10° C. and further stirred at the same temperature for 10 minutes. The cold suspension was filtered and the residue washed with dry toluene. The combined filtrate was cooled to about −5° to −8° C., treated with dry ether (2 ml), followed by slow addition of stannic chloride (1 ml). The light orange-yellow complex, thus formed, was stirred for 30 minutes at about −5° to −8° C. and then for about 16 hours at room temperature.

Toluene was decanted off from the complex and the complex was washed with toluene (10 ml) and reagent grade n-hexane (10 ml), respectively. Slow addition of cold methanol (about 20 ml) to the above cold and stirred complex resulted in the formation of a suspension of 4-nitrobenzyl 3-exomethylene-1-oxo-7-phenoxyacetamidocepham-4-carboxylate. The above suspension was stirred for about 4 hours under ice-bath cooling, filtered, washed with methanol, ether respectively and dried in vacuo to a constant weight. 1.69 g of 4-Nitrobenzyl 3-exomethylene-1-oxo-7-phenoxyacetamidocepham-4-carboxylate with a purity by HPLC of 98.2% was isolated. The yield was therefore 83.9%.

IR Spectrum (KBr): 3380, 1795, 1750, 1695, 1600, 1520, 1350, 1490, 1245, 1195, 1030, 760, 735 cm$^{-1}$.

$^1$H NMR (360 MHz, DMSO-d$_6$, δ-values in ppm, TMS): 3.86, 4.08 (AB$_q$, 2H, C$^2$H$_2$); 4.74 (s, 2H, CH$_2$OC$_6$H$_5$); 5.19 (d, 1H, C$^6$H); 5.44 (s, 2H, OCH$_2$C$_6$H$_4$NO$_2$(p)); 5.33, 5.64, 5.86 (3s, 3H, =CH$_2$+C$^4$H); 5.90 (dd, 1H, C$^7$H); 7.06, 7.41 (2m, 5H, OC$_6$H$_5$); 7.75, 8.34 (AB$_q$, 4H, —C$_6$H$_4$NO$_2$(p)); 8.38 (d, 1H, NH). $^{13}$C NMR (90 MHz, DMSO-d$_6$, ppm): 49.0 (C$^2$); 55.4, 58.3 (C$^7$, C$^4$); 65.7 (C$^6$); 65.8, 66.7 (2 OCH$_2$); 126.0 (=CH$_2$).

Mass Spectrum: CI(NH$_3$) gave MH$^+$=500.

EXAMPLE 3

Preparation of 4-nitrobenzyl 3-exomethylene-1-oxo-7-phenylacetamidocepham-4-carboxylate in the presence of various amounts of molecular sieves The reactions were carried out as described in Example 1 using 1.936 g (purity by HPLC=99%) of 4-nitrobenzyl 2,2-dimethyl-1-oxo-6-phenylacetamidopenam-4-carboxylate, N-chlorophthalimide (0.765 g), toluene (35 ml), stannic chloride (1 ml) and ether (2 ml), in the presence of various amounts of molecular sieves (4A, activated powder, max. grain size 50 μm). The results are given in Table 1.

TABLE 1

| | | 4-Nitrobenzyl 3-exomethylene-1-oxo-7-phenylacetamidocepham-4-carboxylate | | |
|---|---|---|---|---|
| Example | Molecular sieves (g) | Isolated yield (g) | Purity (%) | Yield (%) |
| 3a | 0.988 | — | — | — |
| 3b | 0.395 | 0.035 | 85.5 | 1.6 |
| 3c | 0.208 | 1.1 | 98.0 | 56.6 |
| 3d | 0.100 | 1.34 | 98.0 | 69.0 |
| 3e | 0.048 | 0.85 | 96.0 | 43.0 |
| 1 | 0.147 | 1.38 | 97.5 | 70.9 |

EXAMPLE 4

Preparation of 4-nitrobenzyl 3-exomethylene-1-oxo-7-phenoxyacetamidocepham-4-carboxylate in the presence of various amounts of molecular sieves The reactions were carried out as described in Example 2 using 2.0 g (purity by HPLC =99%) of 4-nitrobenzyl 2,2-dimethyl-1-oxo-6-phenoxyacetamidopenam-4-carboxylate, N-chlorophthalimide (0.765 g), toluene (37 ml), stannic chloride (1 ml) and ether (2 ml), in the presence of various amounts of molecular sieves (4A, activated powder, max. grain size 50 μm). The results are given in Table 2.

TABLE 2

| | | 4-Nitrobenzyl 3-exomethylene-1-oxo-7-phenoxyacetamidocepham-4-carboxylate | | |
|---|---|---|---|---|
| Example | Molecular sieves (g) | Isolated yield (g) | Purity (%) | Yield (%) |
| 4a | 0.400 | 1.59 | 97.0 | 78.0 |
| 4b | 0.200 | 1.66 | 97.5 | 82.0 |
| 4c | 0.100 | 1.69 | 96.5 | 83.0 |
| 2 | 0.150 | 1.69 | 98.2 | 83.9 |

EXAMPLE 5

Preparation of 4-nitrobenzyl 3-exomethylene-1-oxo-7-phenylacetamidoceoham-4-carboxylate in the presence of various types of molecular sieves The reaction was carried out as described in Example 1 using 1.936 g (purity by HPLC=98%) of 4-nitrobenzyl 2,2-dimethyl-1-oxo-6-phenylacetamidopenam-4-carboxylate, N-chlorophthalimide (0.766 g), toluene (36 ml), stannic chloride (1 ml) and ether (2 ml), in the presence of various types of molecular sieves. The results are given in Table 3.

TABLE 3

| | | 4-Nitrobenzyl 3-exomethylene-1-oxo-7-phenylacetamidocepham-4-carboxylate | | |
|---|---|---|---|---|
| Example | Molecular sieves (type) | Isolated yield (g) | Purity (%) | Yield (%) |
| 5a | 3A* | 1.07 | 96.5 | 54.8 |
| 5b | 13X** | 1.20 | 97.0 | 61.3 |
| 1 | 4A | 1.38 | 97.5 | 70.9 |

*Powdered, average grain size 3–5 μm (Janssen Chimica), further dried at 320° C. for 6 hours, 0.150 g.

**Powdered, 325 mesh (Aldrich), further dried at 320° C. for 6 hours, 0.155 g.

EXAMPLE 6

Preparation of 4-nitrobenzyl 3-exomethylene-1-oxo-7-phenoxyacetamidocepham-4-carboxylate in the presence of various types of molecular sieves The reactions were carried out as described in Example 2 using 2.0 g (purity by HPLC =99%) of 4-nitrobenzyl 2,2-dimethyl-1-oxo-6-phenoxyacetamidopenam-4-carboxylate, N-chlorophthalimide (0.765 g), toluene (36 ml), stannic chloride (1 ml) and ether (2 ml), in the presence of various types of molecular sieves. The results are given in Table 4.

TABLE 4

| Example | Molecular sieves (type) | 4-Nitrobenzyl 3-exomethylene-1-oxo-7-phenoxyacetamidocepham-4-carboxylate | | |
|---|---|---|---|---|
| | | Isolated yield (g) | Purity (%) | Yield (%) |
| 6a | 5A* | 1.70 | 97.0 | 82.9 |
| 6b | 3A* | 1.71 | 98.0 | 84.4 |
| 6c | 13X** | 1.68 | 97.0 | 81.7 |
| 2 | 4A | 1.69 | 98.2 | 83.9 |

*Powdered, average grain size 3–5 μm (Janssen Chimica), further dried at 320° C. for 6 hours, 0.152 g.
**Powdered, 325 mesh (Aldrich), further dried at 320° C. for 6 hours, 0.151 g.

EXAMPLE 7

Preparation of 4-nitrobenzyl 3-exomethylene-1-oxo-7-phenylacetamidocepham-4-carboxylate with various refluxing times The reaction was carried out as described in Example 1 using 1.936 g (purity by HPLC=99%) of 4-nitrobenzyl 2,2-dimethyl-1-oxo-6-phenylacetamidopenam-4-carboxylate, N-chlorophthalimide (0.765 g), molecular sieves (4A, activated powder, max. grain size 50 μm; 0.153 g), toluene (35 ml), stannic chloride (1 ml) and ether (2 ml) with various refluxing times. The results are given in Table 5.

TABLE 5

| Example | Refluxing times (min) | 4-Nitrobenzyl 3-exomethylene-1-oxo-7-phenylacetamidocepham-4-carboxylate | | |
|---|---|---|---|---|
| | | Isolated yield (g) | Purity (%) | Yield (%) |
| 7a | 45 | 1.24 | 96.5 | 63.0 |
| 7b | 60 | 1.33 | 96.5 | 67.0 |
| 7c | 80 | 1.40 | 97.0 | 69.0 |
| 2 | 100 | 1.38 | 97.5 | 70.9 |

EXAMPLE 8

Preparation of 4-nitrobenzyl 3-exomethylene-1-oxo-7-phenylacetamidocepham-4-carboxylate (one-pot process)

4-Nitrobenzyl 2,2-dimethyl-1-oxo-6-phenylacetamidopenam-4-carboxylate (1.936 g; purity by HPLC=96%), molecular sieves (4A, activated powder, max. grain size 50 μm; 0.152 g) and N-chlorophthalimide (0.765 g) in dry toluene (36 ml) were quickly heated to reflux for about 100 minutes. The reaction mixture was cooled to about 10° C. and further stirred at the same temperature for 10 minutes. Then, the reaction mixture was cooled to about −10° C., treated with dry ether (2 ml), followed by slow addition of stannic chloride (1 ml). The contents were stirred for 30 minutes at about −5° C. to −8° C. and then for about 16 hours at room temperature.

The reaction mixture was centrifuged, washed with dry toluene and then with reagent grade n-hexane. The wet solid contents, obtained as above, were slowly added to stirred cold methanol (about 25 ml) and further stirred under ice-bath cooling for 4 hours. The reaction contents were filtered, washed with methanol and ether, respectively. The solid contents were stirred with acetonitrile, filtered to remove the molecular sieves and the filtrate was evaporated under reduced pressure. The product was treated with cold methanol (25 ml) and further stirred at room temperature for 4 hours. Thereafter, the reaction mixture was filtered, washed with methanol, with a mixture of methyl isobutyl ketone : diisopropyl ether (1:1) and ether respectively, and dried under vacuum to a constant weight. 1.43 g of 4-Nitrobenzyl 3-exomethylene-1-oxo-7-phenylacetamidocepham-4-carboxylate with a purity by HPLC of 94.5% was isolated. The yield was therefore 73.0%.

EXAMPLE 9

Preparation of 4-nitrobenzyl 3-exomethylene-1-oxo-7-phenoxyacetamidocepham-4-carboxylate (one-pot process)

4-Nitrobenzyl 2,2-dimethyl-1-oxo-6-phenoxyacetamidopenam-4-carboxylate (2.00 g; purity by HPLC=99.9%), molecular sieves (4A, activated powder, max. grain size 50 μm; 0.154 g, Janssen Chimica) and N-chlorophthalimide (0.767 g) in dry toluene (36 ml) were reacted as described in Example 8.

1.64 g of 4-Nitrobenzyl 3-exomethylene-1-oxo-7-phenoxyacetamidocepham-4-carboxylate with a purity by HPLC of 97.0% was isolated. The yield was therefore 79.9%.

EXAMPLE 10

Preparation of 4-nitrobenzyl 3-exomethylene-1-oxo-7-phenylacetamidocepham-4-carboxylate in the presence of molecular sieves fully saturated with water About 18 ml of toluene was distilled off and discarded from a suspension of molecular sieves (4A, activated powder, max. grain size 50 μm; further saturated with water)(0.184 g) in toluene (77 ml). Then 4-nitrobenzyl 2,2-dimethyl-1-oxo-6-phenylacetamidopenam-4-carboxylate (1.936 g; purity by HPLC=98%), N-chlorophthalimide (0.766 g) and toluene (18 ml) were added and the reaction contents were quickly heated to reflux for about 100 minutes. The reaction mixture was cooled to about 10° C. and further stirred at the same temperature for 10 minutes. The cold suspension was filtered and the residue washed with dry toluene. The combined filtrate was cooled to about −10° C., treated with dry ether (2 ml), followed by slow addition of stannic chloride (1 ml). The reaction mixture was stirred for 30 minutes at about −10° C. and then for about 16 hours at room temperature.

The reaction mixture was centrifuged, washed with dry toluene and then with reagent grade n-hexane. The wet solid contents, obtained as above, were slowly added to stirred cold methanol (about 25 ml) and further stirred under ice-bath cooling for 4 hours and filtered. The product was washed with methanol and ether respectively, and dried in vacuum to a constant weight. 1.49 g of 4-Nitrobenzyl 3-exomethylene-1-oxo-7-phenylacetamidocepham-4-carboxylate with a purity by HPLC of 97.0% was isolated. The yield was therefore 76.7%.

EXAMPLE 11

Preparation of 4-nitrobenzyl 3-exomethylene-1-oxo-7-phenylacetamidoceoham-4-carboxylate in the presence of various amounts of molecular sieves partially or fully saturated with water The reactions were carried out as described in Example 10 using 1.936 g (purity by HPLC=98%) of 4-nitrobenzyl 2,2-dimethyl-1-oxo-6-phenylacetamidopenam-4carboxylate, N-chlorophthalimide (0.766 g), toluene (77 ml), stannic chloride (1 ml) and ether (2 ml) in the presence of various amounts of molecular sieves (4A, activated powder, max grain size 50 μm, further saturated with water). 0.184, 0.240, 0.495 and 0.738 g of molecular sieves fully saturated with water (ex. 10, 11c, 11b and 11a, respectively) correspond with 0.150, 0.195, 0.402 and 0.600 g, respectively, of molecular sieves untreated with water. 0.1543 g of molecular sieves partially saturated with water (ex. 11d) corresponds with 0.1512 g of molecular sieves untreated with water. The results are given in Table 6.

TABLE 6

| Example | Molecular sieves saturated with water (g) | 4-Nitrobenzyl 3-exomethylene-1-oxo-7-phenylacetamidocepham-4-carboxylate | | |
|---|---|---|---|---|
| | | Isolated yield (g) | Purity (%) | Yield (%) |
| 11a | 0.738 | 0.56 | 95.5 | 28.2 |
| 11b | 0.495 | 1.46 | 97.5 | 75.4 |
| 11c | 0.240 | 1.45 | 96.5 | 74.0 |
| 11d | 0.1543 | 1.46 | 96.0 | 74.2 |
| 10 | 0.184 | 1.49 | 97.0 | 76.7 |

EXAMPLE 12

Preparation of 4-nitrobenzyl 3-exomethylene-1-oxo-7-phenoxyacetamidocepham-4-carboxylate in the presence of molecular sieves saturated with water About 18 ml of toluene was distilled off and discarded from a suspension of molecular sieves (4A, activated powder, max. grain size 50 μm; further saturated with water)(0.184 g) in toluene (77 ml). Then 4-nitrobenzyl 2,2-dimethyl-1-oxo-6-phenoxyacetamidopenam-4-carboxylate (2.0 g; purity by HPLC=99.9%), N-chlorophthalimide (0.765 g) and toluene (18 ml) were reacted as described in Example 10.

1.72 g of 4-Nitrobenzyl 3-exomethylene-1-oxo-7-phenoxyacetamidocepham-4-carboxylate with a purity by HPLC of 98.5% was isolated. The yield was therefore 85.0%.

EXAMPLE 13

Preparation of 2,2,2-trichloroethyl 3-exomethylene-1-oxo-7-phenylacetamidocepham-4-carboxylate 2,2,2-Trichloroethyl 2,2-dimethyl-1-oxo-6-phenylacetamidopenam-4-carboxylate (1.92 g; purity by NMR=97%), molecular sieves (4A, activated powder, max. grain size 50 μm; 0.152 g) and N-chlorophthalimide (0.765 g) in toluene (36 ml) were quickly heated to reflux for about 100 minutes. The reaction mixture was cooled to about 10° C. and further stirred at the same temperature for 10 minutes. The cold suspension was filtered and the residue washed with dry toluene. The combined filtrate was cooled to about −10° C., treated with dry ether (2 ml), followed by slow addition of stannic chloride (1 ml). The reaction mixture was stirred for 30 minutes at about −10° C. and then for about 16 hours at room temperature.

Thereafter, toluene was decanted off from the complex and then the complex was washed with toluene (10 ml) and reagent grade n-hexane (10 ml) respectively. Slow addition of cold methanol (25 ml) to the above cold and stirred complex resulted in the formation of a suspension of trichloroethyl 3-exomethylene-1-oxo-7-phenylacetamidocepham-4-carboxylate. The above suspension was stirred for 4 hours under ice-bath cooling and filtered. The product was washed with methanol and ether respectively, and dried in vacuum to a constant weight. 1.097 g of 2,2,2-Trichloroethyl 3-exomethylene-1-oxo-7-phenylacetamidocepham-4-carboxylate with a purity by NMR of 94.0% was isolated. The yield was therefore 55.1%.

IR Spectrum (KBr): 3350, 1770, 1748, 1670, 1518, 1200, 1048, 780, 725 $cm^{-1}$.

$^1$H NMR (360 MHz; $CDCl_3$, δ-value in ppm, TMS): 3.57, 3.76 ($AB_q$, 2H, $C^2\underline{H}_2$); 3.60, 3.65 ($AB_q$, 2H, $C\underline{H}_2C_6H_5$); 4.76, 4.86 ($AB_q$, 2H, $C\underline{H}_2CCl_3$); 5.48, 5.80 (2s, 2H, $=CH_2$) en 5.35 (s, 1H, $C^4\underline{H}$); 4.86 (d, 1H, $C^6\underline{H}$); 5.98 (dd, 1$\underline{H}$, $C^7\underline{H}$); 6.93 (d, 1H, N$\underline{H}$); 7.3 (m, 5H, —$C_6H_5$).

$^{13}$C NMR (90 MHz, $CDCl_3$): 43.5 ($ArCH_2$); 49.6 ($C^2$); 55.4, 59.8 ($C^7$, $C^4$); 66.9 ($C^6$); 74.5 ($CH_2CCl_3$); 123.1 ($=CH_2$); 127.5, 129.0, 129.3, 133.8 (aromatic); 165.6, 166.2, 171.5 (3 CO).

Mass Spectrum: $CI(NH_3)$ gave $MH^+ = 479$.

EXAMPLE 14

Preparation of 2,2,2-trichloroethyl 3-exomethylene-1-oxo-7-phenoxyacetamidocepham-4-carboxylate 2,2,2-Trichloroethyl 2,2-dimethyl-1-oxo-6-phenoxyacetamidopenam-4-carboxylate (1.92 g; purity by NMR=97%), molecular sieves (4A, activated powder, max. grain size 50 μm; 0.158 g) and N-chlorophthalimide (0.766 g) in toluene (36 ml) were quickly heated to reflux for about 100 minutes. The reaction mixture was cooled to about 10° C. and further stirred at the same temperature for 10 minutes. The cold suspension was filtered and the residue washed with dry toluene. The combined filtrate was cooled to about −10° C., treated with dry ether (2 ml), followed by slow addition of stannic chloride (1 ml). The reaction mixture was stirred for 30 minutes at about −10° C. and then for about 16 hours at room temperature.

Thereafter toluene was decanted off from the complex and then the complex was washed with toluene (10 ml) and reagent grade n-hexane (10 ml) respectively. Thereafter with stirring, methanol (25 ml) was added to the above reaction product and further stirred for 4 hours under ice-bath cooling. Slow addition of cold methanol resulted in no product isolation. Then most of the methanol was removed under reduced pressure and the reaction contents extracted with ethyl acetate. The combined ethyl acetate extracts were washed twice with 5% aqueous sodium bicarbonate solution, water and dried over anhydrous magnesium sulfate. The dried solution evaporated under reduced pressure and further dried under vacuum to a constant weight to give 1.79 g of 2,2,2trichloroethyl 3-exomethylene-1-oxo-7-phenoxyacetamidocepham-4-carboxylate with a purity by NMR of 75.0%. The yield was therefore 69.0%.

IR Spectrum (KBr): 3385, 3340, 1782, 1750, 1698, 1249, 1060, 1040, 1027, 775, 755, 726 cm$^{-1}$.

$^1$H NMR Spectrum (360 MHz; CDCl$_3$, δ-value in ppm, TMS): 3.61, 3.79 (AB$_q$, 2H, C$^2$H$_2$); 4.54 (s, 2H, C$_6$H$_5$OCH$_2$); 4.75, 4.87 (AB$_q$, 2H, OCH$_2$CCl$_3$); 4.93 (d, 1H, C$^6$H); 5.37, 5.82 (2s, 2H, =CH$_2$); 5.51 (s, 1H, C$^4$H); 6.03 (dd, 1H C$^7$H); 6.8-7.3 (m, 5H, Ar); 8.15 (d, 1H, NH).

$^{13}$C NMR (90 MHz; CDCl$_3$; ppm): 49.6 (C$^2$); 55.5, 58.9 (C$^4$, C$^2$); 66.7 (C$^6$); 66.8 (C$_6$H$_5$OC); 74.5 (OCH$_2$CCl$_3$); 94.2 (CDCl$_3$); 127.2 (=CH$_2$).

Mass Spectrum: CI(NH$_3$) gave MH$^+$=495, MNH$_4^+$=512.

EXPERIMENTS WITHOUT MOLECULAR SIEVES

Preparation of 4-nitrobenzyl 3-exomethylene-1-oxo-7-phenylacetamidoceoham-4-carboxylate a. The reaction was carried out as described in Example 1 using 1.936 g (purity by HPLC=99%) of 4-nitrobenzyl 2,2-dimethyl-1-oxo-6-phenylacetamidopenam-4-carboxylate, N-chlorophthalimide (0.761 g), toluene (35 ml), stannic chloride (1 ml) and ether (2 ml). The only difference was that no molecular sieves were used. No 4-nitrobenzyl 3-exomethylene-1-oxo-7-phenylacetamidocepham-4-carboxylate could be isolated. The HPLC estimation of the reaction mixture showed 0.7% formation of 4-nitrobenzyl 3-exomethylene-1-oxo-7-phenylacetamidocepham-4-carboxylate.

b. The reaction was carried out as described in Example 1 using 1.936 g (purity by HPLC=97.5%) of 4-nitrobenzyl 2,2-dimethyl-1-oxo-6-phenylacetamidopenam-4-carboxylate, N-chlorophthalimide (0.760 g), toluene (35 ml), stannic chloride (1 ml) and ether (2 ml). The only difference was that no molecular sieves were used. The isolated yield of 4-nitrobenzyl 3-exomethylene-1-oxo-7-phenylacetamidocepham-4-carboxylate was 0.778 g with a purity by HPLC of 94% giving a yield of 39.9%.

What is claimed is:

1. A process for the preparation of 2-chlorosulfinylazetidin-4-one of formula II or a pharmaceutically acceptable salt thereof:

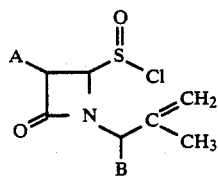

wherein
A is a protected amino group and
is a protected carboxy group, which comprises reacting a corresponding penam sulfoxide ester of the formula III

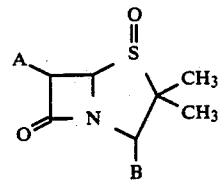

wherein A and B are as defined above, with a N-chloro halogenating agent, in the presence of molecular sieves and, optionally, converting the compound of formula II to a pharmaceutically acceptable salt thereof.

2. A process according to claim 1, wherein the molecular sieves are activated molecular sieves.

3. A process according claim 1, wherein the molecular sieves are in the form of a powder.

4. A process according to claim 1, wherein the molecular sieves have a nominal pore diameter of about 2×10$^{-4}$, to about 12×10$^{-4}$ μm.

5. A process according to claim 1, wherein the molecular sieves have a nominal pore diameter of about 3×10$^{-4}$, or about 4×10$^{-4}$, or about 5×10$^{-4}$, or about 10×10$^{-4}$ μm.

6. A process according to claim 1, wherein the molecular sieves are used in an amount of from about 2.5–40% (w/w), based on the penam sulfoxide ester.

7. A process according to claim 6, wherein the molecular sieves are used in an amount of from about 5–25% (w/w), based on the penam sulfoxide ester.

8. A process according to claim 1, wherein the molecular sieves are partially or fully saturated with water.

9. A process according to claim 1, wherein the N-chloro halogenating agent is N-chloro phthalimide or N-chloro succinimide.

10. A process for the preparation of a 3-methylenecepham compound of formula I or a pharmaceutically acceptable salt thereof

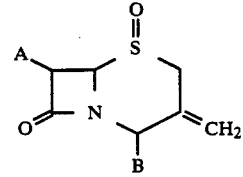

wherein A and B are as defined in claim 1, which comprises reacting a corresponding penam sulfoxide of the formula III

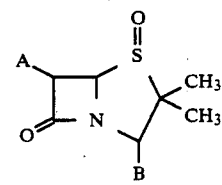

wherein A and B are as defined above, with an N-chloro halogenating agent, in the presence of molecular sieves according to claim 11, isolating a compound of formula II as defined in claim 1 and converting the same into a 3-methylenecepham derivative of formula I and, optionally into a pharmaceutically acceptable salt thereof.

11. A one-pot process for the preparation of a 3-methylenecepham compound of formula I or a pharmaceutically acceptable salt thereof

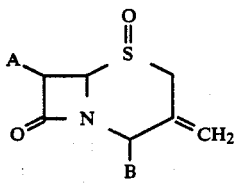
I wherein A and B are as defined in claim 1, which comprises reacting a corresponding penam sulfoxide of the formula III

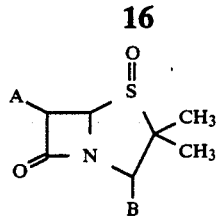
III wherein A and B are as defined above, with an N-chloro halogenating agent, in the presence of molecular sieves, adding an oxo compound and a Lewis acid, isolating the resulting complex and decomposing the same by adding a decomposing alcohol.

12. A process according to claim 1, which includes the additional step of converting the group A and/or the group B to a deprotected amino group and a deprotected carboxy group, respectively.

13. A process according to claim 1, wherein the compound of formula III is 4-nitrobenzyl 2,2-dimethyl-1-oxo-6-phenoxyacetamidopenam-4-carboxylate or 4-nitrobenzyl 2,2-dimethyl-1-oxo-6-phenylacetamidopenam-4-carboxylate.

* * * * *